(12) United States Patent
Collins

(10) Patent No.: US 7,598,089 B2
(45) Date of Patent: Oct. 6, 2009

(54) METHODS AND COMPOSITIONS FOR SEPARATING CELLS

(75) Inventor: Daniel P. Collins, Lino Lakes, MN (US)

(73) Assignee: BioE, Inc., St. Paul, MN (US)

( * ) Notice: Subject to any disclaimer, the term of this patent is extended or adjusted under 35 U.S.C. 154(b) by 356 days.

(21) Appl. No.: 11/406,790

(22) Filed: Apr. 19, 2006

(65) Prior Publication Data

US 2007/0248984 A1   Oct. 25, 2007

(51) Int. Cl.
*G01N 1/18* (2006.01)

(52) U.S. Cl. ............................ 436/177; 435/7.2; 435/2; 436/529; 436/10; 436/16; 436/17; 436/18; 436/63; 436/166; 436/174; 436/176; 436/179

(58) Field of Classification Search ................ 435/7.21, 435/7.23–7.25, 7.5, 2, 40.52, 326, 328, 355, 435/343.1, 344, 372.1, 372.2, 372.3, 7.2; 436/514, 518, 523, 529, 547, 548, 10, 16, 436/17, 18, 63, 64, 166, 176, 177, 179; 530/387.7, 530/388.1, 388.8, 391.1
See application file for complete search history.

(56) References Cited

U.S. PATENT DOCUMENTS

| | | | |
|---|---|---|---|
| 5,773,224 A | 6/1998 | Grandics et al. | |
| 5,840,502 A * | 11/1998 | Van Vlasselaer | 435/7.21 |
| 6,280,622 B1 * | 8/2001 | Goodrich et al. | 210/252 |
| 6,491,917 B1 | 12/2002 | Thomas et al. | |
| 6,544,751 B1 | 4/2003 | Brandwein et al. | |
| 6,949,355 B2 * | 9/2005 | Yamanishi et al. | 435/34 |
| 2003/0027233 A1 | 2/2003 | Collins et al. | |
| 2007/0249047 A1 * | 10/2007 | McKenna et al. | 435/372 |

OTHER PUBLICATIONS

International Search Report and Written Opinion mailed Nov. 20, 2007 in PCT/US07/66935, 10 pages.
Bigbee et al., "Monoclonal antibodies specific for the M- and N-forms of human glycophorin A*," *Molecular Immunology*, 1983, 20(12):1353-1362.
Cole et al., "The EBV-Hybridoma Technique and Its Application to Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Collins, "Cytokine and cytokine receptor expression as a biological indicator of immune activation: important considerations in the development of in vitro model systems," *J. Immunol. Meth.*, 2000, 243:125-145.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4(3):72-79.
Outram et al., "Erythromyeloid lineage fidelity is conserved in erythroleukaemia," *Leukemia Research*, 1988, 12(8):651-657.
Telen and Bolk, "Human red cell antigens. IV. The abnormal sialoglycoprotein of Gerbich-negative red cells," *Transfusion*, 1987, 27:309-314.
Wagner, "Umbilical Cord Blood Stem Cell Transplantation," *Am. J. Ped. Hematol. Oncol.*, 1993, 15(2):169-174.

* cited by examiner

*Primary Examiner*—Gailene R Gabel
(74) *Attorney, Agent, or Firm*—Fish & Richardson P.C.

(57) ABSTRACT

The invention provides compositions and methods for cell separation. These reagents and techniques specifically agglutinate cells via surface antigen recognition and can be used to recover rare cell types in high yield.

20 Claims, No Drawings

METHODS AND COMPOSITIONS FOR SEPARATING CELLS

TECHNICAL FIELD

The present invention relates generally to compositions and methods for separating cells, and more particularly, to compositions and methods for specifically removing erythrocytes from blood-cell containing samples to facilitate enhanced recovery of leukocytes, thrombocytes, stem cells, and other non-erythrocytic components of blood.

BACKGROUND

Isolation of cells for in vitro studies or for applications in cellular therapies usually requires an initial separation of blood cell components mainly based on the bulk depletion of erythrocytes, which comprise >99% of the cellular mass of blood. These techniques for erythrocyte removal are based on hypotonic lysis of erythrocytes, density gradient separation, or enhanced centrifugal sedimentation using heta starch. Hypotonic lysis, while useful in low volume in vitro studies, is inefficient and impractical for the large volumes of blood tissues processed for cellular therapies.

Density-gradient separation relies on small differences in the density of different cell types causing them to segregate at different levels in a fluid medium of variable density. Differences in density between the cell types can be small, and individual cells types can be heterogeneous in size and density. Consequently, particular cell types can become distributed throughout a density-gradient medium rather than precisely segregating at a discrete area in the density medium, resulting in poor recovery of desired cells and/or contamination with undesired cell types. In procedures that enrich for rare blood cell types such as hematopoietic progenitor cells, density-gradient sedimentation generally results in poor yields. For example, using conventional density-gradient methods to isolate progenitor cells (e.g., $CD34^+$ hematopoietic stem cells) from umbilical cord blood reportedly results in a significant loss of the desired stem cells. See e.g., Wagner, J. E., *Am J Ped Hematol Oncol* 15:169 (1993). As another example, using conventional density-gradient methods to isolate lymphocytes reportedly results in selective loss of particular lymphocyte subsets. See e.g., Collins, D. P., *J Immunol Methods* 243:125 (2000).

An additional method for removing erythrocytes from blood includes using heta starch, which stimulates the formation of erythrocyte aggregates that sediment more rapidly than leukocyte components when sedimented at 50×g in a centrifuge. While this method is non-toxic and 'safe' for the recipient, its performance in the recovery of important cell types (e.g., hematopoietic stem cells) is highly variable depending upon factors such as temperature, age of sample (post-collection) prior to processing, cellularity of sample, and volume of sample. These factors, with respect to umbilical cord blood, for example, can often result in poor recovery of stem cells and diminution of the engraftment potential of the cord blood cells, increasing the risk for transplant failure.

Increasing the recovery of rare cell types from donor tissue could dramatically improve the success of transplant and immune therapies (e.g., bone marrow transplants, stem cell-based gene therapy, and immune cell therapy), the success of which apparently is related to the actual number of the cells being used for therapy.

SUMMARY

The invention is based on the discovery of compositions and methods for specifically removing erythrocytes from biological samples such that non-erythroid cell subsets, including leukocytes, thrombocytes, and stem cells including hematopoietic stem cells, circulating stem cells, and multi-lineage progenitor cells, can be recovered. Without being bound to a particular mechanism, compositions of the invention can fractionate blood samples by specifically aggregating erythrocytic cells via surface antigen recognition and stimulating the enhanced sedimentation of erythrocytes at 1×g, allowing even rare cell types to be recovered in relatively high yield from the supernatant. The disclosed compositions and methods can be used, for example, to efficiently prepare cells for tissue culture, immunophenotypic characterization, other diagnostic testing, further purification, and therapeutic administration.

In one aspect, the invention features a composition that includes dextran; anti-glycophorin A antibody; heparin; and a calcium chelator. The composition further can include phosphate buffered saline. The pH of the composition can be between 6.8 to 7.8. The composition further can include serum albumin (e.g., bovine serum albumin or human serum albumin). The concentration of the serum albumin can be about 0.5% to about 5%. The anti-glycophorin A antibody can be monoclonal and can be an IgM antibody or an IgG antibody. The anti-glycophorin A antibody can be an anti-human glycophorin A antibody. The concentration of the anti-glycophorin A antibody can be about 0.001 mg/L to about 15 mg/L. The calcium chelator can be EDTA (e.g., 0.1 mM to 5 mM EDTA). The calcium chelator can be EGTA (e.g., 0.1 mM to 5 mM EGTA). The calcium chelator can be sodium citrate (e.g., 0.05M to 0.5 M sodium citrate).

In another aspect, the invention features a kit that includes a blood collection vessel and a cell separation composition described herein. The blood collection vessel can be a blood bag or a vacuum tube.

The invention also features a method for separating cells. The method includes contacting a blood cell-containing sample with a cell separation composition described herein; allowing the sample to partition into an agglutinate and a supernatant phase at 1×g; and recovering the cells. The sample can be a human blood cell-containing sample, a peripheral blood sample, an umbilical cord sample, or a bone marrow sample. The cells can be recovered from the supernatant phase.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features compositions and methods for separating cells. As described herein, the compositions specifically aggregate erythrocytic cells via surface antigen recognition and stimulate the enhanced sedimentation of erythrocytes at 1×g. Non-erythrocytic cells, including, for example, leukocytes, thrombocytes, and stem cells can be recovered from the supernatant phase of the fractionated blood sample.

Cell Separation Compositions

A cell separation composition in accord with the invention can contain dextran, heparin, a calcium chelator, and anti-glycophorin A antibodies. Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Typically, soluble dextran having a molecular weight of 500,000 (e.g., from 400,000 to 550,000, Sigma Chemical Co., St. Louis) is used in compositions of the invention.

Cell separation compositions of the invention also contain an anticoagulant such as heparin. Heparin can prevent clotting and non-specific cell loss associated with clotting in a high calcium environment. Heparin can be supplied as a heparin salt (e.g., sodium heparin, lithium heparin, or potassium heparin).

A calcium chelator also is included in a composition of the invention. Without being bound to a particular mechanism, calcium chelators can prevent platelet aggregation and depletion, and also prevent the stimulation of granulocyte adhesion molecule activation (CD11b) resulting in aggregation, degranulation and depletion of granulocytes. Suitable calcium chelators include, for example, ethylenediaminetetraacetic acid (EDTA), ethyleneglycol-bis(β-aminoethyl)-N,N,N',N'-tetraacetic Acid (EGTA), or sodium citrate. Typically, a calcium chelator is present at about 0.1 mM to 5.0 M. For example, EDTA or EDTA can be present at about 0.1 mM to 5 mM (e.g., 0.25 to 2.5 mM, 0.5 to 2.0 mM, 0.75 to 1.5 mM., or 1.0 mM) and sodium citrate can be present at 0.5 to 5.0 M (e.g., 0.5 to 4.0 M, 0.75 to 3.75 M, 1.0 M, 1.0 to 4.0 M, 1.5 to 4.5 M, 2.0 to 5.0 M, 1.0 to 2.0 M, 2.0 to 3.0 M, 3.0 to 4.0 M, or 4.0 to 5.0 M). In addition to inhibiting granulocyte activation, the calcium chelators also act as anticoagulants.

A cell separation composition also includes antibodies against (i.e., that have specific binding affinity for) glycophorin A. Anti-glycophorin A antibodies can facilitate the removal of red cells from solution by causing homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 Isotype), YTH89.1 (Rat IgG2b Isotype), and E4 (Murine IgM Isotype). See e.g., M. Vanderlaan et al., Molecular Immunology 20:1353 (1983); Telen M. J. and Bolk, T. A., Transfusion 27:309 (1987); and Outram S. et al., Leukocyte Research. 12:651 (1988).

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., Nature, 1975, 256:495, the human B-cell hybridoma technique (Kosbor et al., Immunology Today 4:72 (1983); Cole et al., Proc. Natl. Acad. Sci. USA 80:2026 (1983)), and the EBV-hybridoma technique (Cole et al., "Monoclonal Antibodies and Cancer Therapy," Alan R. Liss, Inc., pp. 77-96 (1983)).

Antibodies can be of any immunoglobulin class including IgG, IgM, IgE, IgA, IgD, and any subclass thereof. Antibodies of the IgG and IgM isotypes are particularly useful in cell separation compositions of the invention. Pentameric IgM antibodies contain more antigen binding sites than IgG antibodies and can be particularly useful for cell separation reagents. Typically, antibodies are provided in a cell separation composition at a concentration between about 0.001 and about 15 mg/L (e.g., between 0.25 to 10, 0.25 to 1, 0.5 to 2, 1 to 2, 4 to 8, 5 to 10 mg/L). For example, anti-glycophorin A antibodies can be provided at 0.05 mg/L.

In some embodiments, a cell separation composition further includes serum albumin (e.g., human or bovine serum albumin). Typically, 0.001 to 1.0 g/L of serum albumin is used. For example, 0.005 to 0.5, 0.0075 to 0.25, 0.01 to 0.02, 0.1 to 0.5, 0.4 to 0.8, or 0.0125 g/L of serum albumin can be used. Typically, the composition also contains a buffer (e.g., phosphate buffered saline (PBS)) and has a pH ranging from 6.8 to 7.8 (e.g., 7.4). Other buffers such as MOPS (3-(N-Morpholino)propanesulfonic acid) or HEPES (4-(2-Hydroxyethyl)piperazine-1-ethanesulfonic acid) also can be used.

Compositions of the invention can be obtained by combining the components (e.g., dextran, PBS, anti-human glycophorin A, bovine or human serum albumin, anticoagulant, and calcium chelator) in water and then stirring the mixture for about 1 to about 30 minutes or until a solution is obtained. For example, 20 g/L dextran, 100 mL/L 10× PBS, 0.05 g/mL anti-human glycophorin A, 0.0125 g/L bovine serum albumin, 1 mL/L heparin (e.g., 10,000 units/mL sodium heparin), and 1 mM EDTA can be combined at room temperature using water to bring the composition to the correct volume and the pH of the composition can be adjusted with sodium hydroxide (e.g., 4N sodium hydroxide).

Methods of Using Cell Separation Compositions

Cells can be separated by contacting a blood cell-containing sample and allowing the sample to partition into an agglutinate and a supernatant phase at 1×g. Cells can be recovered from the supernatant or the agglutinate. The disclosed compositions can be used to separate cells from a variety of blood-cell containing samples, including peripheral blood (e.g., obtained by venipuncture), umbilical cord blood (e.g., obtained post-gravida), and bone marrow (e.g., from aspirate). For example, erythrocytes can be selectively agglutinated using cell separation compositions containing dextran, anti-glycophorin A antibody, heparin, and a calcium chelator, allowing non-erythrocytic blood cell components to be recovered from the solution phase (i.e., the supernatant). Thus, agglutinated cells (e.g., erythrocytes) partition away from unagglutinated cells, which remain in solution.

The disclosed compositions and methods can be used to isolate and enrich for a variety of cell types, including, for example, T lymphocytes, T helper cells, T suppressor cells, B cells, hematopoietic stem cells, circulating stem cells (e.g., embryonic or non-embryonic stem cells), circulating fetal cells in maternal circulation, and circulating metastatic tumor cells. The disclosed compositions can be used to agglutinate erythrocytes of any mammal, including humans, non-human primates, rodents, swine, bovines and equines.

The disclosed compositions can be used, for example, to efficiently prepare cells for tissue culture, immunophenotypic characterization, other diagnostic testing, further purification, and therapeutic administration. The disclosed compositions and methods can be used in the context of allogenic and autologous transplantation.

Cell Separation Kits

A cell separation composition can be combined with packaging material and sold as a kit. The components of a cell separation composition can be packaged individually or in combination with one another. In some embodiments, the packaging material includes a blood collection vessel (e.g., blood bag or vacuum tube). The packaging material included in a kit typically contains instructions or a label describing how the cell separation composition can be used to agglutinate erythrocytes. Components and methods for producing such kits are well known.

The invention is further described in the following examples, which do not limit the scope of the invention described in the claims.

EXAMPLES

Example 1

Separating Blood Cells

Equal volumes of a cell separation reagent (see Table 1) and a citrate anti-coagulated peripheral blood sample (25 mL each) were combined in a 50 ml conical tube. Tubes were gently mixed on a rocker platform (or by gentle inversion) for 30 to 45 minutes at room temperature. Tubes were stood upright in a rack for 30 to 50 minutes to permit agglutinated cells to partition away from unagglutinated cells, which remained in solution, and to allow sedimentation. Without disturbing the agglutinate, a pipette was used to recover unagglutinated cells from the supernatant. Recovered cells were washed in phosphate buffered saline (PBS) plus 1% bovine serum albumin or human serum albumin (HSA), or tissue culture medium.

TABLE 1

| Cell Separation Composition | |
| --- | --- |
| Dextran | 20 g/l |
| Dulbecco's Phosphate Buffered Saline (10×) | 100 ml/l |
| Anti-human glycophorin A (murine IgM monoclonal Antibody, clone 2.2.2.E7) | 0.05 g/ml |
| Bovine Serum Albumin | 12.5 g/mL |
| Sodium Heparin (10,000 units/ml) | 1 ml/l |
| EDTA | 1 mM |

As indicated in Table 2, high percentages of white blood cells (average 89.6%, range 81.6%-95.7%) and platelets (average 90.7%, range 85.4%-95.9) were recovered and over 99.1% of the erythrocytes were removed from the blood sample. Similar results were obtained when HSA was used in place of bovine serum albumin.

TABLE 2

| Recovery of Leukocytes and Platelets from Normal Adult Peripheral Blood | | | |
| --- | --- | --- | --- |
|  | Donor 1 | Donor 2 | Donor 3 |
| WBC Recovery | 95.7% | 91.4% | 81.6% |
| Lymphocyte Recovery | 94.2% | 92.9% | 77.1% |
| Monocyte Recovery | 93.3% | 95.8% | 86.1% |
| Granulocyte Recovery | 97.2% | 89.7% | 82.5% |
| Platelet Recovery | 85.4% | 91% | 95.9% |
| CD3+ T-cell Recovery | 94.5% | 96% | 77.5% |
| Erythrocyte Depletion | 99.2% | 99.1% | 99.2% |

Example 2

Comparison of Leukocyte Recovery

The recovery of leukocytes from blood samples was compared between the cell separation composition of Example 1 and the cell separation composition from Example 2 of U.S. patent application Ser. No. 10/094,456 (the '456 application). The cell separation composition of the '456 application contained 20 g/L dextran (average molecular weight 413,000); 100 ml/L Dulbecco's PBS (10×); 1 mL/L sodium heparin (10,000 units/mL); 50 ml/L Hank's balanced salt solution (pH 7.2-7.4); and 1.0 mg/L anti-human glycophorin A (murine IgM monoclonal antibody clone E4). The blood cells were separated as indicated in Example 1 above. As shown in Table 3, when a peripheral blood sample was separated using the cell separation composition of Example 1 from the present application, recovery was higher for total white blood cells, lymphocytes, monocytes, granulocytes, platelets, and CD3+ T cells than when the blood sample was separated using the cell separation composition of the '456 application.

TABLE 3

Comparison of Recovery of Leukocytes and Platelets
from Normal Adult Peripheral Blood

|  | Donor 4 | | Donor 5 | | Donor 6 | | Donor 7 | |
| --- | --- | --- | --- | --- | --- | --- | --- | --- |
|  | '456 appln | Ex. 1 | '456 appln | Ex. 1 | '456 appln | Ex. 1 | '456 appln | Ex. 1 |
| WBC Recovery | 68.19% | 83.38% | 61.32% | 76.84% | 74.87% | 82.95% | 77.18% | 89.73% |
| Lymphocyte Recovery | 75.62% | 83.68% | 74.55% | 84.47% | 61.48% | 69.74% | 64.32% | 77.23% |
| Monocyte Recovery | 65.4% | 85.59% | 45.83% | 65.85% | 67.91% | 75.83% | 89.38% | 85.16% |
| Granulocyte Recovery | 65.7% | 83.1% | 61.14% | 74.02% | 81.91% | 90.07% | 85.7% | 100% |
| Platelet Recovery | 81.68% | 92.45% | 80.89% | 86.21% | 92.47% | 97.66% | 89.56% | 95.63% |
| CD3+ T-cell Recovery | 73.16% | 77.86% | 76.15% | 84.96% | 61.83% | 69.07% | 80.56% | 89.05% |
| Erythrocyte Depletion | 99.8% | 99.41% | 99.73% | 99.27% | 99.61% | 99.27% | 99.7% | 99.3% |

A further comparison was done based on the recovery of total nucleated cells (TNC) and hematopoietic stem cells (CD34+) from human umbilical cord blood samples (collected within 24-48 hrs) using the method set out in Example 1 above. As indicated in Table 4, recovery of TNC and hematopoietic stem cells was enhanced when the formulation from Example 1 of the present application was used.

TABLE 4

Comparison of Recovery of TNC and Hematopoietic Stem
Cells (CD34+) from Human Umbilical Cord Blood

|  | '456 application | | Example 1 | |
| --- | --- | --- | --- | --- |
| Donor | TNC | CD34+ | TNC | CD34+ |
| 1 | 83.65% | 125.4%* | 90.4% | 127.38%* |
| 2 | 55.72% | 79.6% | 69.45% | 77.62% |
| 3 | 51.92% | 68.48% | 68.54% | 74.49% |
| 4 | 78.68% | 92.12% | 91.52% | 98.22% |
| 5 | 52% | 82.73% | 60.02% | 92.76% |

*Due to the difficultly in accurately determining the exact numbers of stem cells in some samples of whole cord blood which can comprise less than 0.2% of nucleated cells, recoveries sometimes are expressed as greater than 100%.

OTHER EMBODIMENTS

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A cell separation reagent comprising:
 a) dextran;
 b) anti-glycophorin A antibody;
 c) heparin;
 d) serum albumin; and
 e) ethylenediaminetetraacetic acid (EDTA) wherein dextran, anti-glycophorin A antibody, heparin, serum albumin, and EDTA are in solution.

2. The reagent of claim 1, further comprising phosphate buffered saline.

3. The reagent of claim 1, wherein the pH of said reagent is between 6.8 to 7.8.

4. The reagent of claim 1, wherein said serum albumin is bovine serum albumin.

5. The reagent of claim 1, wherein said serum albumin is human serum albumin.

6. The reagent of claim 1, wherein said anti-glycophorin A antibody is monoclonal.

7. The reagent of claim 1, wherein said anti-glycophorin A antibody is an IgM antibody or an IgG antibody.

8. The reagent of claim 1, wherein said anti-glycophorin A antibody is an anti-human glycophorin A antibody.

9. The reagent of claim 1, wherein the concentration of said anti-glycophorin A antibody is about 0.001 mg/L to about 15 mg/L.

10. The reagent of claim 1, wherein the concentration of said serum albumin is about 0.5% to about 5%.

11. The reagent of claim 1, wherein the concentration of EDTA is 0.1 mM to 5 mM.

12. A kit comprising a blood collection vessel and the cell separation reagent of claim 1.

13. The kit of claim 12, wherein said blood collection vessel is a blood bag.

14. The kit of claim 12, wherein said blood collection vessel is a vacuum tube.

15. A method for separating cells, said method comprising
 a) contacting a blood cell-containing sample with the cell separation reagent of claim 1;
 b) allowing said sample of step a) to partition into an agglutinate and a supernatant phase at 1 xg; and
 c) recovering said cells from the agglutinate or the supernatant phase.

16. The method of claim 15, wherein said sample is a human blood cell-containing sample.

17. The method of claim 15, wherein said sample is a peripheral blood sample.

18. The method of claim 15, wherein said sample is an umbilical cord sample.

19. The method of claim 15, wherein said sample is a bone marrow sample.

20. The method of claim 15, wherein said cells are recovered from said supernatant phase.

* * * * *

UNITED STATES PATENT AND TRADEMARK OFFICE
CERTIFICATE OF CORRECTION

PATENT NO.         : 7,598,089 B2
APPLICATION NO.    : 11/406790
DATED              : October 6, 2009
INVENTOR(S)        : Daniel Collins It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 356 days Delete the phrase "by 356 days" and insert -- by 526 days --

Signed and Sealed this

Fourth Day of May, 2010

David J. Kappos
*Director of the United States Patent and Trademark Office*